(12) United States Patent
Qiu et al.

(10) Patent No.: US 11,712,820 B2
(45) Date of Patent: Aug. 1, 2023

(54) INJECTION MOLDING METHOD FOR DEGRADABLE INTRAVASCULAR STENT WITH FLEXIBLE MOLD CORE STRUCTURE

(71) Applicant: Beijing Institute of Technology, Beijing (CN)

(72) Inventors: Tianyang Qiu, Beijing (CN); Wei Jiang, Beijing (CN); Hongjun Wang, Beijing (CN); Tianfeng Zhou, Beijing (CN); Wenxiang Zhao, Beijing (CN); Pei Yan, Beijing (CN); Zhiqiang Liang, Beijing (CN); Zhibing Liu, Beijing (CN); Lijing Xie, Beijing (CN); Li Jiao, Beijing (CN); Xibin Wang, Beijing (CN)

(73) Assignee: Beijing Institute of Technology, Beijing (CN)

( * ) Notice: Subject to any disclaimer, the term of this patent is extended or adjusted under 35 U.S.C. 154(b) by 0 days.

(21) Appl. No.: 17/348,057

(22) Filed: Jun. 15, 2021

(65) Prior Publication Data
US 2022/0032509 A1   Feb. 3, 2022

(51) Int. Cl.
| | |
|---|---|
| *B29C 33/50* | (2006.01) |
| *B29C 33/48* | (2006.01) |
| *B29C 45/03* | (2006.01) |
| *A61F 2/915* | (2013.01) |
| *B29L 23/00* | (2006.01) |

(52) U.S. Cl.
CPC .......... *B29C 33/505* (2013.01); *B29C 33/485* (2013.01); *B29C 45/03* (2013.01); *A61F 2/915* (2013.01); *B29L 2023/007* (2013.01)

(58) Field of Classification Search
CPC ... B29C 45/0025; B29C 45/261; B29C 45/44; B29C 45/4471; B29C 33/485; B29C 33/505; A61F 2/91; A61F 2/915; A61F 2/82
See application file for complete search history.

(56) References Cited

U.S. PATENT DOCUMENTS

2003/0114919 A1 * 6/2003 McQuiston ............... A61F 2/07
623/1.15

* cited by examiner

*Primary Examiner* — Yunju Kim
(74) *Attorney, Agent, or Firm* — Marcus C. Dawes

(57) ABSTRACT

Disclosed is an injection molding method for a degradable intravascular stent with a flexible mold core structure. The injection molding method includes the following steps: Step 1, winding a metal rod with a flexible metal film, and applying an inward bending stress to the flexible metal film; Step 2, fixing the flexible metal film to the metal rod, and processing a complementary structure of the degradable intravascular stent on the surface of the flexible metal film; Step 3, performing injection molding processing; Step 4, ending the injection molding, removing the mating body of the flexible metal film and the metal rod and the degradable intravascular stent formed on the surface of the flexible metal film by injection molding, performing cooling, separating the metal rod from the flexible metal film, withdrawing the metal rod, and then removing the flexible metal film to obtain a formed degradable intravascular stent.

7 Claims, 5 Drawing Sheets

INJECTION MOLDING METHOD FOR DEGRADABLE INTRAVASCULAR STENT WITH FLEXIBLE MOLD CORE STRUCTURE

CROSS REFERENCE TO RELATED APPLICATION(S)

This patent application claims the benefit and priority of Chinese Patent Application No. 202010749187.0, filed on Jul. 30, 2020, the disclosure of which is incorporated by reference herein in its entirety as part of the present application.

TECHNICAL FIELD

The present disclosure relates to the technical field of intravascular stent processing, and in particular, to an injection molding method for a degradable intravascular stent with a flexible mold core structure.

BACKGROUND ART

Intravascular stent implantation is one of the most conventional and effective methods for the treatment of cardiovascular blockage problems at present. A new generation of degradable intravascular stent can be self-degraded and absorbed after completing the dilation and dredging functions of a stenotic vessel, does not have any side effects, and can reduce the incidence probability of late complications, such as restenosis and inflammation in the stent. The material of the degradable intravascular stent is usually a biologically absorbable high-molecular polymer, and can be formed at one time in an injection molding manner. A stent injection molding process at present mainly designs a mold structure integrally. After injection molding is completed, the mold is separated from the stent through the design of a sliding block.

In the prior art, the manufacturing of the degradable intravascular stent can be designed. However, there are several problems as follows: firstly, the stent is difficult to demold, and the stent is tightly bonded to a mold after the injection molding is completed, so the stent is difficultly separated from the mould, and the damage and fracture of the stent are easily caused in a separating process; secondly, the problem of deformation after the stent is demolded is serious; because the mold is in an integrated design, the stent needs to be demolded before the temperature decreases; the stent is prone to serious deformation due to the influence of heat expansion and cold contraction after demolding, which affects its accuracy. Therefore, there is an urgent need for a novel mold structure design, so that it can give consideration to a plurality of problems of demolding, deformation after demolding, and the like.

SUMMARY

In order to solve the above-mentioned technical problems, the present disclosure provides an injection molding method for a degradable intravascular stent with a flexible mold core structure, which solves the problems that the degradable intravascular stent is difficult to demold, easily deformed, and easily damaged and fractured in an injection molding processing process.

In order to achieve the above-mentioned objective, the present disclosure provides the following solution:

The present disclosure provides an injection molding method for a biodegradable intravascular stent with a flexible mold core structure, including the following steps:

Step 1, winding a metal rod with a flexible metal film, and applying an inward bending stress to the flexible metal film before fixing the flexible metal film and the metal rod;

Step 2, fixing the flexible metal film to the metal rod, and processing a complementary structure of the degradable intravascular stent on the surface of the flexible metal film;

Step 3, assembling a mating body of the flexible metal film and the metal rod with a mold sleeve of an injection molding machine, and performing injection molding processing of the degradable intravascular stent;

Step 4, ending the injection molding, removing the mating body of the flexible metal film and the metal rod and the degradable intravascular stent formed on the surface of the flexible metal film by injection molding, performing cooling, separating the metal rod from the flexible metal film, withdrawing the metal rod, where at this time, the flexible metal film will curl inwards, and then removing the flexible metal film to obtain a formed degradable intravascular stent.

Preferably, in step 2, the flexible metal film is fixed to the metal rod through multiple bolts.

Preferably, in step 2, the complementary structure of the degradable intravascular stent is processed on the surface of the flexible metal film by a laser processing or high-speed milling processing method.

Preferably, in step 4, the flexible metal film is separated from the metal rod by removing the multiple bolts for connecting the flexible metal film and the metal rod.

Preferably, the flexible metal film is an aluminum film or a copper film.

Preferably, the outside diameter of the degradable intravascular stent is D1, and D1=3 to 3.5 mm; the wall thickness of the degradable intravascular stent is T1, and T1=0.15 to 0.2 mm.

Preferably, the thickness of the flexible metal film is T2, and T2=0.3 to 0.4 mm; the diameter of the metal rod is D2, and D2=D1−2*T2.

Compared with the prior art, the present disclosure achieves the following technical effects:

In the injection molding method for a degradable intravascular stent with a flexible mold core structure provided by the present disclosure, the processed mating body of the flexible metal film and the metal rod and the mould sleeve of the injection molding machine are assembled to perform injection molding processing on the degradable intravascular stent; a wrapped part of the degradable intravascular stent is separated from the mould sleeve of the injection molding machine and can be removed; the degradable intravascular stent is removed after cooling, so that the problem of deformation of the degradable intravascular stent caused by heat expansion and cold contraction is avoided. The inward bending stress is designed for the flexible metal film, so after the metal rod is removed, the flexible metal film will curl inwards and cannot expand outwards, which facilitates demolding and avoids the damage to the degradable intravascular stent, thereby protecting the structure of the degradable intravascular stent. The metal rod and the flexible metal film can be reassembled and reused. In addition, the method can be used for performing injection molding processing on the degradable intravascular stents with different shapes and different structures on the surfaces, and meanwhile, can realize the processing of micro-structures on an inner wall of the degradable intravascular stent.

BRIEF DESCRIPTION OF THE DRAWINGS

To describe the technical solutions in the embodiments of the present disclosure or in the prior art more clearly, the following briefly describes the accompanying drawings required for describing the embodiments or the prior art. Apparently, the accompanying drawings in the following description are merely some embodiments of the present disclosure, and those of ordinary skill in the art may derive other drawings from these accompanying drawings without creative efforts.

Figure 1:
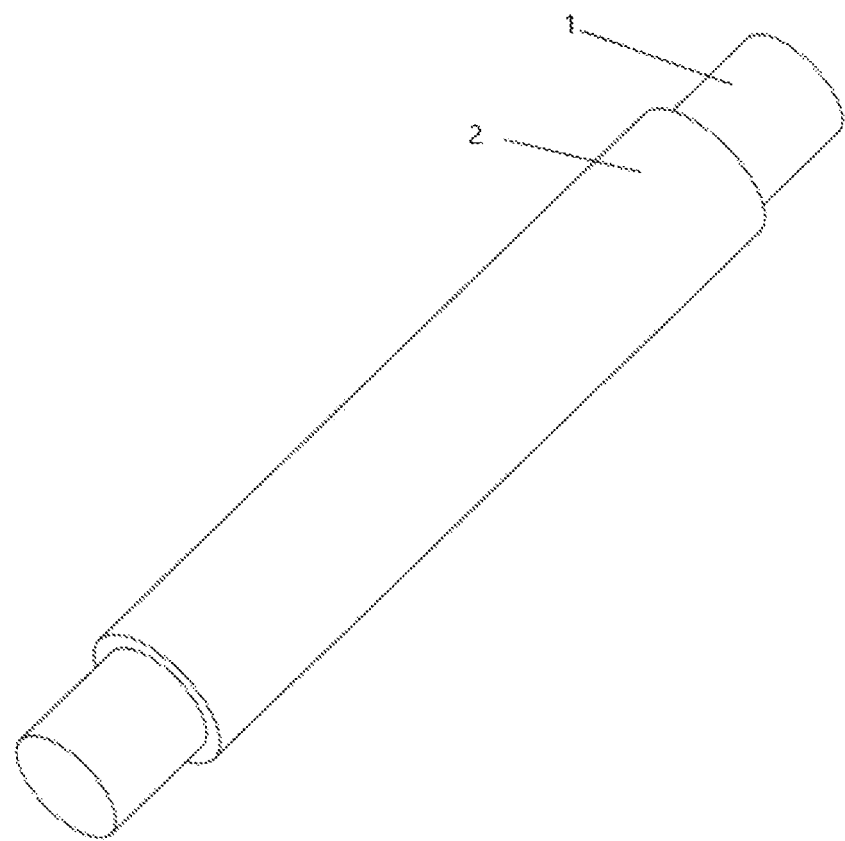
FIG. 1 is a schematic diagram of Step 1 of an injection molding processing method for a degradable intravascular stent with a flexible mold core structure provided by the present disclosure.

Description of reference numerals: 1—metal rod; 2—flexible metal film; 3—degradable intravascular stent.

DETAILED DESCRIPTION OF THE EMBODIMENTS

The technical solution in the embodiments of the present disclosure will be clearly and completely described herein below with reference to the accompanying drawings in the embodiments of the present disclosure. Apparently, the described embodiments are merely part rather than all of the embodiments of the present disclosure. On the basis of the embodiments of the present disclosure, all other embodiments obtained by those of ordinary skill in the art without creative work fall within the scope of protection of the present disclosure.

The objective of the present disclosure is to provide an injection molding method for a degradable intravascular stent with a flexible mold core structure, which solves the problems that the degradable intravascular stent is difficult to demold, easily deformed, and easily damaged and fractured in an injection molding processing process.

In order to make the above objective, features, and advantages of the present disclosure become more apparent and more comprehensible, the present disclosure is further described in detail below with reference to the accompanying drawings and specific implementation manners.

Figure 2:
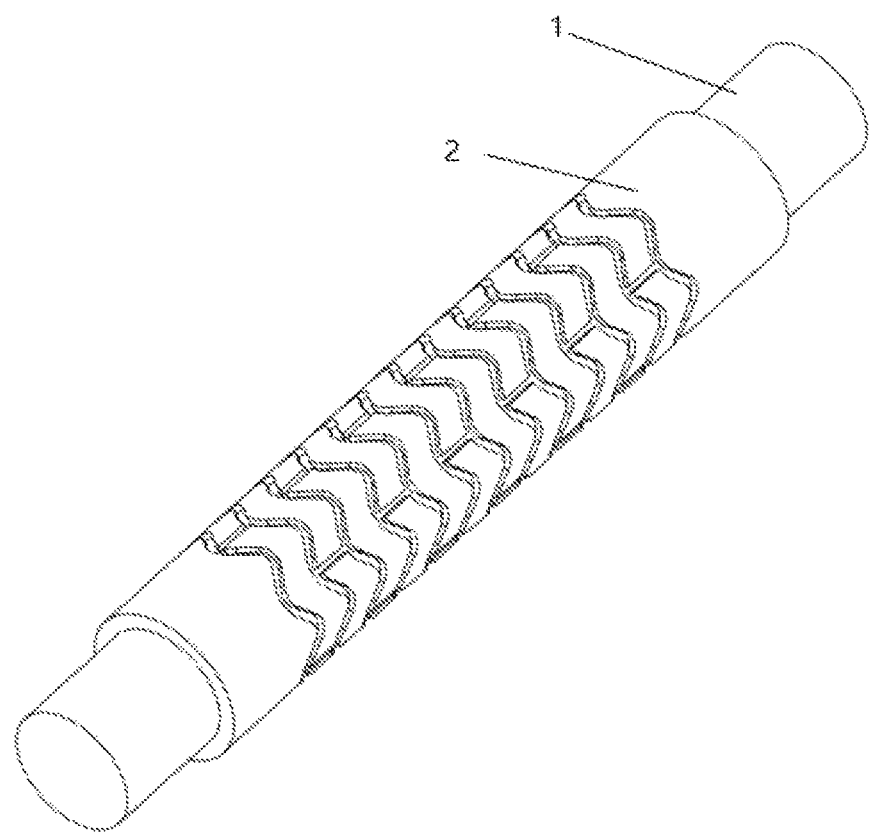
FIG. 2 is a schematic diagram of Step 2 of the injection molding processing method for a degradable intravascular stent with a flexible mold core structure provided by the present disclosure.
Figure 3:
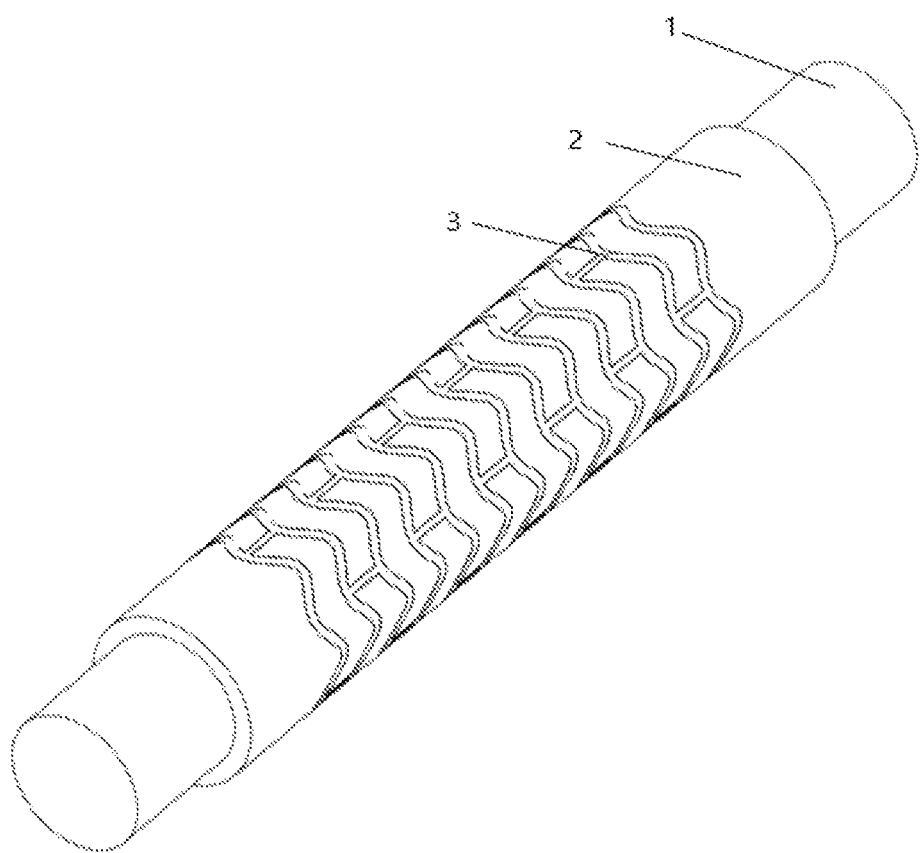
FIG. 3 is a schematic diagram of Step 3 of the injection molding processing method for a degradable intravascular stent with a flexible mold core structure provided by the present disclosure.
Figure 4:
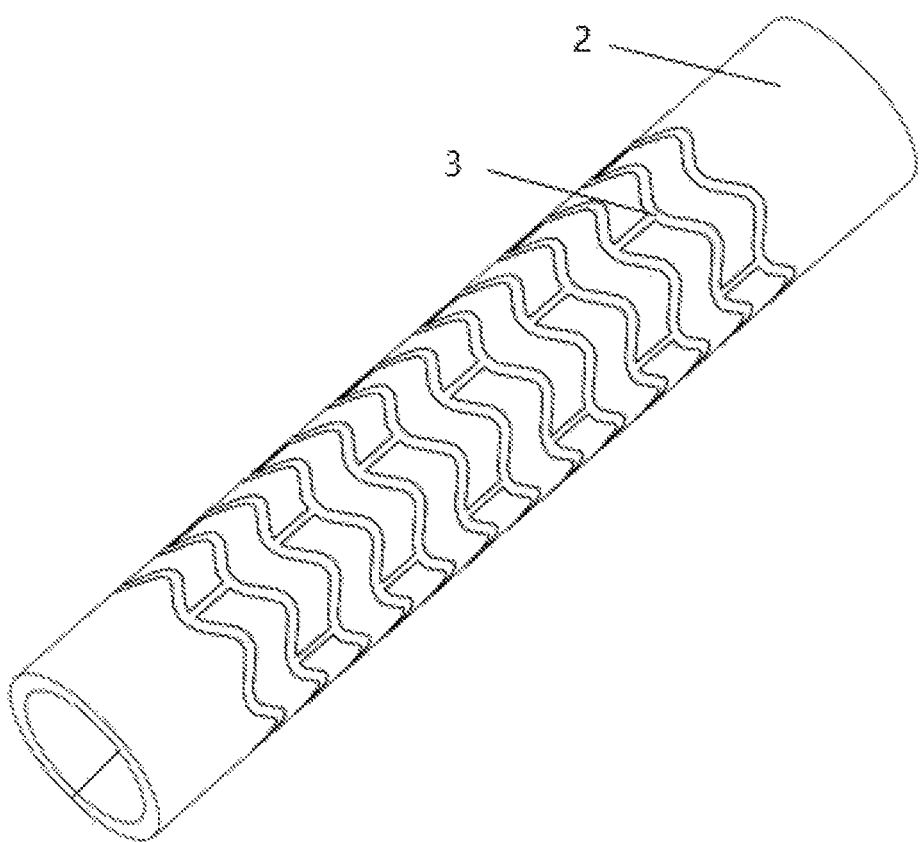
FIG. 4 is a schematic diagram of Step 4 of the injection molding processing method for a degradable intravascular stent with a flexible mold core structure provided by the present disclosure.
Figure 5:
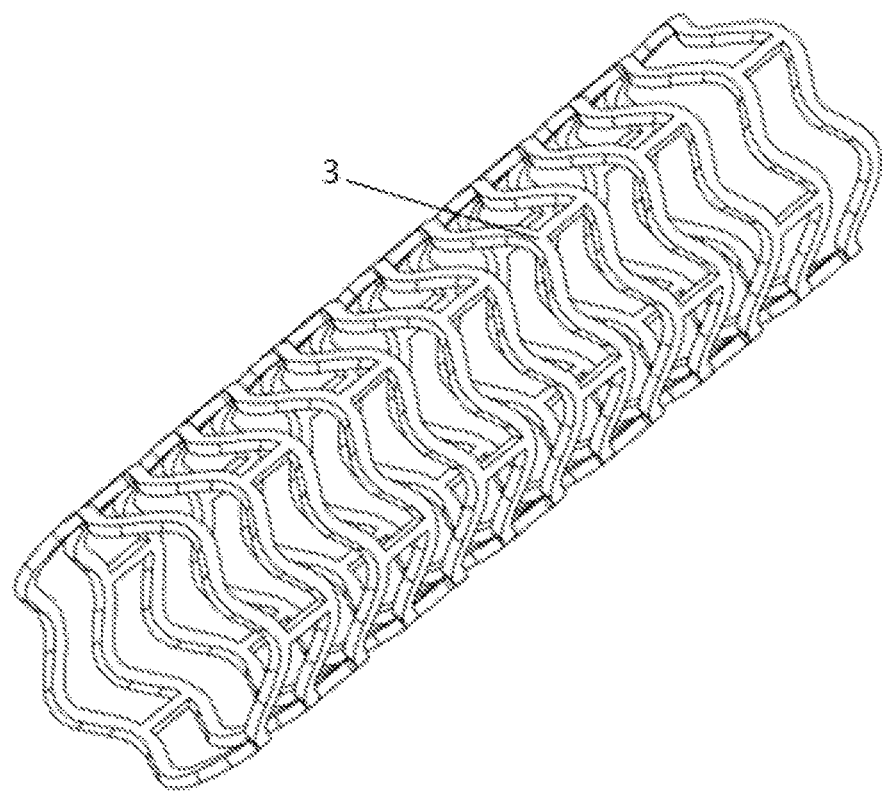
FIG. 5 is a schematic structural diagram of the degradable intravascular stent of the present disclosure.

The present embodiment provides an injection molding method for a degradable intravascular stent with a flexible mold core structure, including the following steps:

Step 1, as shown in FIG. 1, a metal rod 1 is wound with a flexible metal film 2, and an inward bending stress is applied to the flexible metal film 2 before the flexible metal film 2 and the metal rod 1 are fixed, so that the flexible metal film 2 retracts inwards after being separated from the metal rod 1;

Step 2, as shown in FIG. 2, the flexible metal film 2 is fixed to the metal rod 1, and a complementary structure of the degradable intravascular stent 3 is processed on the surface of the flexible metal film 2;

Step 3, as shown in FIG. 3, a processed mating body of the flexible metal film 2 and the metal rod 1 is assembled with a mold sleeve of an injection molding machine, and injection molding processing of the degradable intravascular stent 3 is performed. Specifically, the operation process is consistent with a conventional intravascular stent injection molding process;

Step 4, the injection molding is ended, the mating body of the flexible metal film 2 and the metal rod 1 and the degradable intravascular stent 3 formed on the surface of the flexible metal film by injection molding are removed and cooled, the metal rod 1 is separated from the flexible metal film 2, the metal rod 1 is withdrawn, as shown in FIG. 4, the flexible metal film 2 will curl inwards at this time, and then the flexible metal film 2 is removed, as shown in FIG. 5, to obtain a formed degradable intravascular stent 3.

The mating body of the flexible metal film 2 and the metal rod 1 in the present embodiment is a separated flexible mold core and is matched with the mould sleeve of the injection molding machine for use. After injection molding processing, a wrapped part of the degradable intravascular stent 3 is separated from the mould sleeve of the injection molding machine and can be removed; the degradable intravascular stent 3 is removed after cooling, so that the problem of deformation of the degradable intravascular stent 3 caused by heat expansion and cold contraction is avoided. The inward bending stress is designed for the flexible metal film 2. After the metal rod 1 is removed, the flexible metal film 2 will curl inwards and cannot expand outwards, which facilitates demolding and avoids the damage to the degradable intravascular stent 3, thereby protecting the structure of the degradable intravascular stent 3.

The metal rod 1 and the flexible metal film 2 in the present embodiment can be reassembled and reused. In addition, the complementary structure of the degradable intravascular stent 3 does not need to be processed in second use, so that the processing efficiency is improved in subsequent use. In addition, the degradable intravascular stents 3 with different shapes corresponding to the complementary structures can be processed by processing the complementary structures with different shapes on the flexible metal film 2. Meanwhile, the degradable intravascular stents 3 with different sizes can be processed by using separate flexible mold cores and mould sleeves of the injection molding machine with different sizes. It can be seen that the method can be used for injection molding processing of the degradable intravascular stents 3 with different shapes and different structures on the surfaces, and meanwhile, can realize the processing of micro-structures on an inner wall of the degradable intravascular stent 3.

Specifically, in step 2, the flexible metal film 2 is fixed to the metal rod 1 through multiple bolts. In Step 4, the flexible metal film 2 is separated from the metal rod 1 by removing the multiple bolts for connecting the flexible metal film 2 and the metal rod 1. The flexible metal film 2 and the metal rod 1 are convenient to connect and detach by using the bolts, which improves the work efficiency.

Specifically, in Step 2, the complementary structure of the degradable intravascular stent 3 is processed on the surface of the flexible metal film 2 by a laser processing or high-speed milling processing method.

Specifically, the flexible metal film 2 is an aluminum film or a copper film.

Specifically, the outside diameter of the degradable intravascular stent 3 is D1, and D1=3 to 3.5 mm; the wall thickness of the degradable intravascular stent 3 is T1, and T1=0.15 to 0.2 mm.

Specifically, the thickness of the flexible metal film 2 is T2, T2=0.3 to 0.4 mm; the diameter of the metal rod 1 is D2, and D2=D1−2*T2.

In the present specific embodiment, the outside diameter of the degradable intravascular stent 3 is 3.5 mm and the wall thickness of 0.15 mm; the thickness of the flexible metal film 2 is 0.3 mm; the diameter of the metal rod 1 is 2.9 mm.

In the present disclosure, specific examples are applied to illustrate the principle and implementation manner of the present disclosure. The description of the above embodiments is only used to help understand the method and core idea of the present disclosure. Meanwhile, for those of ordinary skill in the art, there will be changes in the specific implementation manner and scope of application according to the idea of the present disclosure. In conclusion, the contents of the present specification shall not be construed as a limitation to the present disclosure.

What is claimed is:

1. An injection molding method for a degradable intravascular stent with a flexible mold core structure, comprising the following steps:
   Step 1, winding a metal rod with a flexible metal film, and applying an inward bending stress to the flexible metal film before fixing the flexible metal film and the metal rod;
   Step 2, fixing the flexible metal film to the metal rod, and processing a complementary structure of the degradable intravascular stent on the surface of the flexible metal film;
   Step 3, assembling the flexible mold core structure of the flexible metal film and the metal rod with a mold sleeve of an injection molding machine, and performing injection molding processing;
   Step 4, ending the injection molding, removing the flexible mold core structure of the flexible metal film and the metal rod and the degradable intravascular stent formed on the surface of the flexible metal film by injection molding, performing cooling, separating the metal rod from the flexible metal film, and withdrawing the metal rod, wherein the flexible metal film will curl inwards; then removing the flexible metal film to obtain a formed degradable intravascular stent.

2. The injection molding method for a degradable intravascular stent with a flexible mold core structure according to claim 1, wherein in Step 2, the flexible metal film is fixed to the metal rod through multiple bolts.

3. The injection molding method for a degradable intravascular stent with a flexible mold core structure according to claim 1, wherein in Step 2, the complementary structure of the degradable intravascular stent is processed on the surface of the flexible metal film by a laser processing or high-speed milling processing method.

4. The injection molding method for a degradable intravascular stent with a flexible mold core structure according to claim 2, wherein in Step 4, the flexible metal film is separated from the metal rod by removing the multiple bolts for connecting the flexible metal film and the metal rod.

5. The injection molding method for a degradable intravascular stent with a flexible mold core structure according to claim 1, wherein the flexible metal film is an aluminum film or a copper film.

6. The injection molding method for a degradable intravascular stent with a flexible mold core structure according to claim 1, wherein the outside diameter of the degradable intravascular stent is D1, and D1=3 to 3.5 mm; the wall thickness of the degradable intravascular stent is T1, and T1=0.15 to 0.2 mm.

7. The injection molding method for a degradable intravascular stent with a flexible mold core structure according to claim 6, wherein the thickness of the flexible metal film is T2, T2=0.3 to 0.4 mm; the diameter of the metal rod is D2, and D2=D1−2*T2.

* * * * *

UNITED STATES PATENT AND TRADEMARK OFFICE
CERTIFICATE OF CORRECTION

| | | |
|---|---|---|
| PATENT NO. | : 11,712,820 B2 | |
| APPLICATION NO. | : 17/348057 | |
| DATED | : August 1, 2023 | |
| INVENTOR(S) | : Tianyang Qiu et al. | |

It is certified that error appears in the above-identified patent and that said Letters Patent is hereby corrected as shown below:

On the Title Page

Item (30) please add:
-- Jul. 30, 2020 (CN).....202010749187.0 --

Signed and Sealed this
Third Day of October, 2023

Katherine Kelly Vidal
*Director of the United States Patent and Trademark Office*